(12) United States Patent
Glover et al.

(10) Patent No.: US 7,781,632 B2
(45) Date of Patent: Aug. 24, 2010

(54) INTEGRATED PROCESSES FOR MAKING DETERGENT RANGE ALKYLBENZENES FROM C5-C6-CONTAINING FEEDS

(75) Inventors: Bryan K. Glover, Algonquin, IL (US); Stephen W. Sohn, Arlington Heights, IL (US); Mark G. Riley, Hinsdale, IL (US); Dean E. Rende, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/511,617

(22) Filed: Jul. 29, 2009

(65) Prior Publication Data
US 2010/0004497 A1 Jan. 7, 2010

Related U.S. Application Data

(62) Division of application No. 11/608,137, filed on Dec. 7, 2006, now Pat. No. 7,683,226.

(60) Provisional application No. 60/751,869, filed on Dec. 20, 2005.

(51) Int. Cl.
C07C 2/58 (2006.01)
C07C 5/02 (2006.01)
C07C 5/32 (2006.01)

(52) U.S. Cl. .................. 585/323; 585/446; 585/259; 585/654; 585/502

(58) Field of Classification Search ............. 585/323, 585/446, 259, 654, 502
See application file for complete search history.

(56) References Cited

U.S. PATENT DOCUMENTS

| | | | | |
|---|---|---|---|---|
| 4,524,235 A * | 6/1985 | Banks et al. | ............. | 585/646 |
| 5,196,625 A * | 3/1993 | Threlkel et al. | ............. | 585/513 |
| 5,276,231 A * | 1/1994 | Kocal et al. | ............. | 585/323 |
| 2004/0176655 A1 * | 9/2004 | Ayoub et al. | ............. | 585/324 |

* cited by examiner

*Primary Examiner*—Thuan Dinh Dang
(74) *Attorney, Agent, or Firm*—Arthur E Gooding

(57) ABSTRACT

Integrated processes for making detergent range alkylbenzenes from $C_5$-$C_6$-containing feeds involve feed pretreatment and/or selective hydrogenation to enable acceptable quality alkylbenzene production at attractive capital and operating costs.

15 Claims, 3 Drawing Sheets

US 7,781,632 B2

INTEGRATED PROCESSES FOR MAKING DETERGENT RANGE ALKYLBENZENES FROM C5-C6-CONTAINING FEEDS

CROSS-REFERENCE TO RELATED APPLICATION

This application is a Division of U.S. application Ser. No. 11/608,137 filed Dec. 7, 2006, which claims benefit of U.S. Provisional Application No. 60/751,869, filed Dec. 20, 2005.

FIELD OF THE INVENTION

This processes disclosed herein pertain to integrated processes for making alkylbenzenes suitable for use in detergent applications from $C_5$-$C_6$-containing feeds such as derived from Fischer-Tropsch syntheses or naphtha range petroleum fractions.

BACKGROUND TO THE INVENTION

Alkylbenzenes (phenyl-alkanes), especially where the alkyl group has 9 to 14 carbon atoms, have found many utilities, the most prominent of which is to make alkylbenzene sulfonates for use in laundry detergents and similar products. Alkylbenzenes are prepared by the alkylation of benzenes with mono-olefins of the desired molecular weight and configuration of the sought alkyl group. Typically these olefins are derived from a kerosene range fraction from a petroleum refining operation. This fraction is a paraffin-containing fraction and is subjected to dehydrogenation to generate the sought olefins.

In some instances it may be desired to locate an alkylbenzene facility at a location where a kerosene fraction is not readily available, or other commercial uses for a kerosene fraction render it less economically attractive as a feedstock for making alkylbenzenes. In these instances the ability to use alternative feedstocks is highly desirable.

Alternative feedstocks include other petroleum fractions, especially naphtha range fractions, and synthesized hydrocarbons such as Fischer-Tropsch materials. These raw materials have a lower molecular weight than the sought olefins for alkylation and accordingly must be subjected to a dimerization or a metathesis to generate olefins of suitable chain length (detergent range olefins). Numerous processes have been disclosed for preparing detergent olefins from these alternative feedstocks. See, for instance, WO 2004/072005, WO 2004/072006, and U.S. Patent Application Publications 2004/0030209, 2004/0176655, and 2004/0199035.

In order for alternative feedstocks to be viable as a source of detergent range olefins, not only must the synthesized olefin meet configurational requirements such as degree and type of branching, but also, the process must be technically feasible and economically competitive. By way of illustration, US 2004/0176655 discloses that the presence of oxygenated compounds and dienes is deleterious to the process and accordingly the feedstock is hydrogenated prior to a dehydrogenation to generate olefins for a dimerization. While this step effectively removes oxygenates and dienes, it also hydrogenates any olefins present in the feedstock and thus represents an operational inefficiency. US 2004/0030209 discloses, inter alia, preparing an olefin mixture of pentene and hexene for dimerization by the metathesis of a $C_4$ olefin mixture. Butadiene and acetylenic compounds are removed by a selective hydrogenation.

SUMMARY OF THE INVENTION

Process embodiments are provided for making alkylbenzenes from feeds containing $C_5$ and $C_6$ paraffins that have enhanced operational economics and yet provide alkylbenzenes of acceptable quality for commercial use including for sulfonation to produce detergents. Thus, alkylbenzenes can be prepared from alternative, and often less expensive, feedstocks such as naphtha range fractions and Fischer-Tropsch synthesized hydrocarbons.

In order to achieve these benefits, the processes integrate the pretreatment of the $C_5$ and $C_6$-containing feeds with the unit operations for generating detergent range olefins containing $C_{10}$ to $C_{12}$ olefins, and the production and refining of alkylbenzenes made from the detergent range olefins. The integrated process embodiments use at least one of three integrated steps. One is removal of oxygenates from the $C_5$ and $C_6$-containing feeds using a lower alcohol or diol extractant to avoid the necessity of a severe hydrogenation of the feed that not only destroys the oxygenates but also any existing olefinic unsaturation in the feed. Thus, the second integration step is enabled which is to introduce a feed containing $C_5$ and $C_6$ paraffins and olefins into a chain growth reaction zone (dimerization or metathesis which may be in combination with oligomerization) for producing the detergent range olefins prior to dehydrogenation of the paraffins in the feed. In the third integration step, a selective hydrogenation is used to convert diolefins to mono-olefins. By having removed the oxygenates, a selective hydrogenation is sufficient to provide acceptable alkylbenzene product. The selective hydrogenation may occur between a dehydrogenation to produce olefins from the feed containing $C_5$ and $C_6$ paraffins and the formation of the detergent range olefins, or the selective hydrogenation may occur after the formation of the detergent range olefins. A particularly attractive aspect of the process embodiments is that by the selective hydrogenation of the dehydrogenation product, the dehydrogenation can be conducted at higher conversion conditions that inherently also increase the formation of diolefins. Moreover, this preferred aspect of the process embodiments facilitates the refining of the alkylbenzene product since virtually no paraffins in the $C_{10}$ to $C_{12}$ range are generated. These higher molecular weight paraffins would typically require a dedicated distillation column operating at subatmospheric pressure for removal from alkylbenzenes.

One of the broad aspects of the integrated process embodiments for producing detergent range alkylbenzenes from paraffinic feedstock comprises:

a) subjecting a feedstock predominantly comprising $C_5$ and $C_6$ paraffins to dehydrogenation conditions to provide a dehydrogenated product that comprises $C_5$ and $C_6$ mono-olefins and a minor amount of diene;

b) reacting the dehydrogenated product of step a under chain growth conditions to provide a detergent range olefin product comprising $C_{10}$ to $C_{12}$ mono-olefins;

c) selectively hydrogenating at least one of the dehydrogenated product of step a and the detergent range olefin product of step b to reduce diene content;

d) alkylating benzene with at least a portion of the detergent range olefin product having been subjected to selective hydrogenation of step c under alkylation conditions including a stoichiometric excess of benzene to olefin to provide an alkylation effluent comprising alkylbenzene and benzene; and e) separating benzene from the alkylation effluent from the alkylbenzene and recycling at least a portion of the benzene to step d.

Another broad aspect of the integrated process embodiments for producing detergent range alkylbenzenes from paraffinic feedstock comprises:

a) subjecting a feedstock predominantly comprising $C_5$ and $C_6$ paraffins and containing $C_5$ and $C_6$ mono-olefins to chain growth reaction conditions for converting $C_5$ and $C_6$ mono-olefins to $C_{10}$ to $C_{12}$ mono-olefins to provide a reaction product containing $C_5$ and $C_6$ paraffins and $C_{10}$ to $C_{12}$ mono-olefins;

b) subjecting the reaction product to distillation to provide a higher boiling fraction containing $C_{10}$ to $C_{12}$ mono-olefins and a lower boiling fraction comprising $C_5$ and $C_6$ paraffins;

c) subjecting at least a portion of the lower boiling fraction of step b to dehydrogenation conditions to provide a dehydrogenated product comprising $C_5$ and $C_6$ mono-olefins;

d) recycling at least a portion of the dehydrogenated product to step a;

e) alkylating benzene with at least a portion of the higher boiling fraction of step b under alkylation conditions including a stoichiometric excess of benzene to olefin to provide an alkylation effluent comprising alkylbenzene and benzene; and f) separating benzene from the alkylation effluent from the alkylbenzene and recycling at least a portion of the benzene to step e.

Yet another broad aspect of the integrated process embodiments for producing detergent range alkylbenzenes from paraffinic feedstock comprises:

a) contacting a feedstock predominantly comprising $C_5$ and $C_6$ paraffins and oxygenated compounds with a liquid extractant comprising at least one of alcohol or diol of 1 to 3 carbon atoms per molecule and a minor amount of water under extraction conditions to provide a deoxygenated feedstock having a reduced concentration of oxygenated compounds and spent extractant;

b) regenerating and recycling to step a at least a portion of the spent extractant as liquid extractant;

c) dehydrogenating the deoxygenated feedstock in a dehydrogenation zone and recovering therefrom a dehydrogenated product comprising $C_5$ and $C_6$ mono-olefins;

d) reacting the dehydrogenated product of step a under chain growth conditions to provide a detergent range olefin product comprising $C_{10}$ to $C_{12}$ mono-olefins;

e) alkylating benzene with at least a portion of the detergent range olefin product under alkylation conditions including a stoichiometric excess of benzene to olefin to provide an alkylation effluent comprising alkylbenzene and benzene; and f) separating benzene from the alkylation effluent from the alkylbenzene and recycling at least a portion of the benzene to step d.

In preferred aspects of the process embodiments, the detergent range olefin product used for benzene alkylation is substantially free of paraffins having 9 or more carbon atoms per molecule, e.g., less than about 0.5, preferably less than about 0.1, mass-percent of paraffins having 9 or more carbon atoms per molecule is present in the detergent range olefin. Thus, the separation of alkylbenzene from the alkylation effluent can be effected in a cost effective manner. Where paraffins having 9 or more carbon atoms per molecule are present, processes for recovering alkylbenzenes have relied upon a paraffin distillation column for purification of the alkylbenzenes. Moreover, these distillation columns are typically operated at subatmospheric pressures, often below about 20 kPa(absolute) (hereinafter kPa(a)) (2.9 psi(absolute) (hereinafter psi(a))), to avoid temperatures that can result in degradation of the alkylbenzene product. These preferred aspects of this embodiment, by not requiring a separation of paraffins having 9 or more carbon atoms per molecule from the alkylbenzene product, provide for reduced capital and operating costs.

In another preferred aspect of the process embodiments, the alkylation is conducted in the presence of a paraffinic component having between 4 and 7, preferably 5 to 6, carbon atoms per molecule to assist in moderating the exothermic alkylation reaction. Preferably, the paraffinic component is provided to the alkylation reaction in a mole ratio to detergent range olefin of between about 1:1 and 20:1. The paraffinic component is readily separated from the alkylbenzene by distillation to provide a benzene and paraffin-containing fraction that can be recycled to the alkylation reaction.

In other preferred aspects of this embodiment, the dehydrogenation of the feed containing $C_5$ and $C_6$ paraffins, is conducted at higher conversions to olefins. Higher conversions generate greater amounts of dienes and cyclics. Preferred integrated processes can tolerate the greater concentrations of dienes and cyclics in the dehydrogenation effluent due to the selective hydrogenation and the separation of the detergent range olefins from lower boiling components which include cyclics. Cyclics generally comprise benzene with some cyclopentadiene, naphthenes and toluene possibly also being formed. The separated detergent range olefins preferably contain less than about 0.1, more preferably less than about 0.01, mass-percent cyclics. Advantageously, benzene can be recovered to provide at least a portion of the benzene for the alkylation.

DETAILED DESCRIPTION

Figure 1:
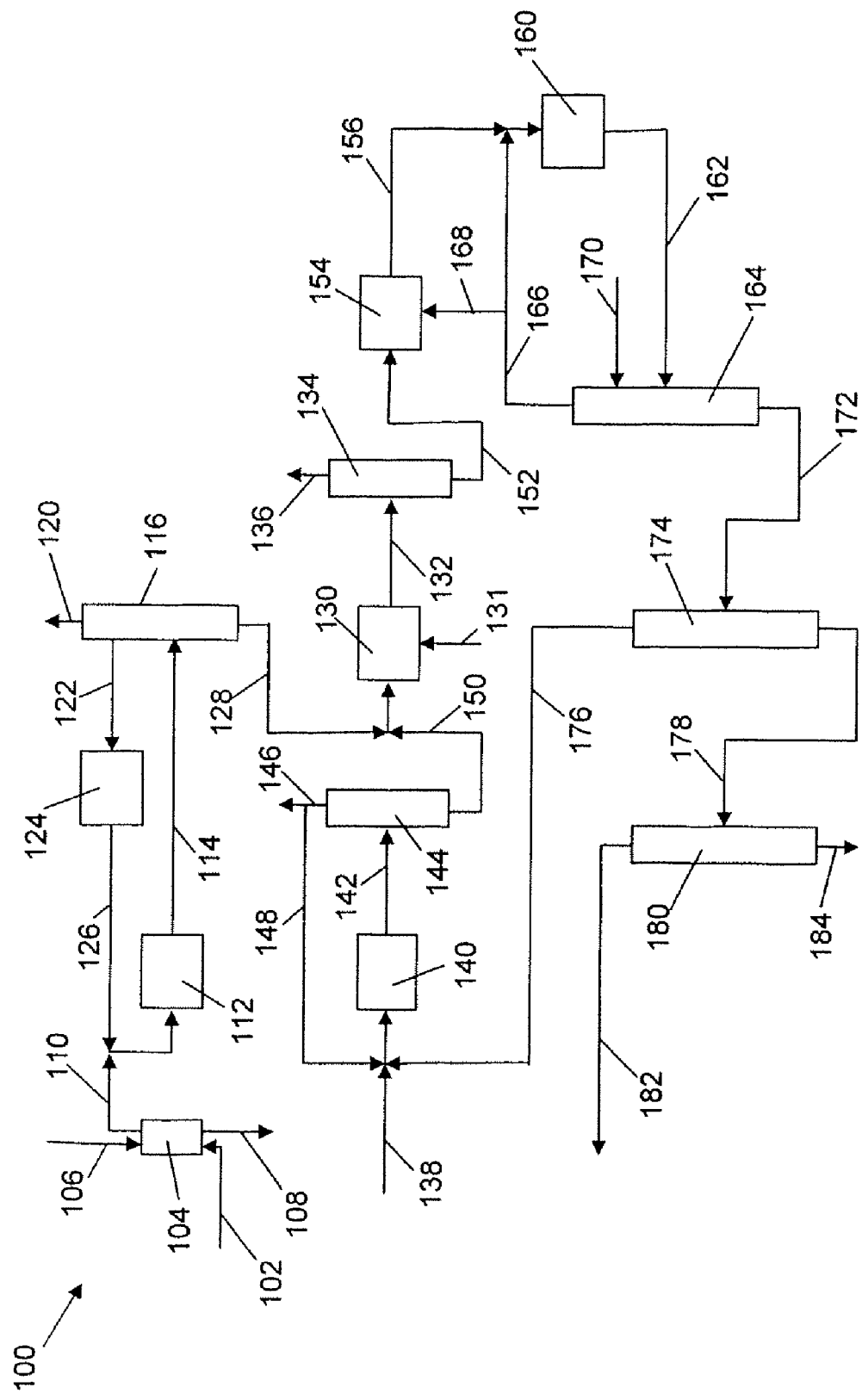
FIG. 1 is a schematic depiction of an apparatus for making alkylbenzenes in which a synthesized $C_5$-$C_6$-containing feed is dimerized and the dimerized feed is used to supplement a detergent-range olefin stream as a feed to an alkylation reactor.

The process embodiments relate to the manufacture of alkylbenzenes suitable for detergent applications from lower molecular weight paraffins, i.e., feedstocks predominantly comprising $C_5$ and $C_6$ paraffins. One source for such feedstocks is from naphtha range fractions from petroleum refining. As branched paraffins and naphthenes are generally preferred for gasoline, normal $C_5$ and $C_6$ paraffins typically have less value to the refiner. However, they tend to be preferred feeds for alkylbenzene manufacture due to the linearity sought for alkylbenzenes used in making detergents. Thus, while the process embodiments can use naphtha range fractions, advantageously a portion of the naphtha fraction is used which contains a greater concentration of normals. This preferred feed may thus be derived from a separation of the naphtha range fraction or may be from a process unit operation involved in gasoline refining such as the effluent from an isomerization unit. Thus, a benefit of the process embodiments can be the up-grading of naphtha range fractions by selectively removing the low octane normal hydrocarbons for use in making detergent range olefins. The separation of normal hydrocarbons from naphtha range fractions is described in, for instance, Stephen W. Sohn, UOP Molex Process for Production of Normal Paraffins, Handbook of Petroleum Refining Processes, Second Edition, Editor Robert A. Meyers, McGraw-Hill, New York, USA (1997) at pp. 10.75 to 10.77. Another source of feedstocks predominantly comprising $C_5$ and $C_6$ paraffins is from synthesis processes such as a Fischer-Tropsch process.

While the feedstocks used in the process embodiments will have different compositions depending upon the source of the feedstocks, the feedstock will nevertheless be predominantly composed of $C_5$ and $C_6$ paraffins. As used herein, a feedstock is predominantly composed of a material when the feedstock contains about 50 mass-percent or more of the material. The feedstocks will likely also contain hydrocarbons of higher and lower carbon numbers. Typically the feedstocks will have the following compositions:

| Component | Typical, mass-percent | Preferred, mass-percent |
| --- | --- | --- |
| $C_4$ | 0.0 to 10 | 0.0 to 5 |
| $C_5$ and $C_6$ paraffins | 50 to 100 | 70 to 100 |
| $C_5$ and $C_6$ olefins | 0 to 50 | 0 to 30 |
| $C_7+$ | 0 to 20 | 0 to 10 |
| Aromatics | 0 to 10 | 0 to 5 |
| Oxygenates | 0 to 3 | 0 to 1 |
| Dienes | 0 to 2 | 0 to 1 |

In the broad aspects of this embodiment wherein the feedstock contains both $C_5$ and $C_6$ paraffins and $C_5$ and $C_6$ monoolefins and is fed to a dimerization or metathesis reactor prior to dehydrogenation, the olefins generally comprise at least about 1, and preferably about 1 to 50, often between about 15 and 30, and in some cases from about 2 to 10, mass-percent of the feedstock. The feedstock may be combined with at least a portion of the product of a dehydrogenation prior to being subjected to chain growth conditions for dimerization or metathesis, or it may be subjected to chain growth conditions to convert at least a portion of the olefinic component to higher carbon number olefins prior to combination with product from the dehydrogenation. In either event, at least a portion of the olefins in the feedstock are consumed and not passed to the dehydrogenation. Not only is a portion of the olefins in the feedstock effectively used, but also, the concentration of olefins in the stream to be dehydrogenated is reduced. As the dehydrogenation is effected by equilibria, enhanced efficiencies in net conversion of paraffins to olefins can be realized.

In the broad aspects of this embodiment where the feedstock contains oxygenated components such as alcohols, aldehydes, ketones, ethers, acids and esters, the oxygenated components may be present in amounts up to about 10 mass-percent. Normally, the oxygenates are present in the range of about 0.001 to 10 mass-percent. More than one oxygenate may be present. The extraction in accordance with this aspect of the embodiment often will yield a feedstock containing less than about 1000, and preferably less than about 200, and sometimes even below 20, parts per million by mass (ppm-mass) oxygenates. See, for instance, Jansen, et al., "Novel Approach Using Methanol/Water Extraction for Hydrocarbon/Oxygenate Separation", presented at the Extractive Separations Topical Conference AIChE Annual Meeting, San Francisco, Calif., November, 2003, for background on extractive separation processes for removing oxygenates from paraffins and olefins.

The extraction is effected using a liquid extractant comprising at least one of alcohol or diol of 1 to 3 carbon atoms per molecule and a minor amount of water under extraction conditions. As used herein, a fluid has a minor amount of a material when the fluid contains about 25 mass-percent or less of the material. The alcohols and diols may be one or more of ethanol, 1-propanol, 2-propanol, ethylene glycol, propylene glycol and 1,3-propanediol, and preferably methanol. The amount of water present in the extractant is usually less than about 25 mass-percent although more water can be present, little benefit is normally seen in using the higher concentrations of water. Most often water is present in the range of about 2 to 15, say, 3 to 10, mass-percent.

Suitable extraction conditions maintain the extractant and the feedstock in liquid phase during the extraction. Usually the extraction is conducted at temperatures in the range of from about 15° C. (59° F.) to 150° C. (302° F.), preferably 30° (86° F.) to 120° C. (258° F.), and pressures of from about 100 kPa(a) (14.5 psi(a)) to 5000 kPa(a) (725 psi(a)), frequently, from about 150 kPa(a) (21.8 psi(a)) to 1000 kPa(a) (145 psi(a)). The extraction operation may be operated in any convenient manner. Normally the contact time is between about 5 seconds and 10 minutes as sufficient to provide the desired reduction in oxygenate content. The extraction may be conducted in a liquid-liquid extraction column. The column may, if desired, contain packing to assist in liquid-liquid contact. The extraction can also be effected in a vessel in which the liquid streams are agitated.

The feedstock is contained in the raffinate and can be recovered by any suitable means such as extraction with water or sorption, can be used to remove residual alcohol or diol from the feedstock. Normally the feedstock will contain less than about 20,000 mass-ppm alcohol or diol after such stripping or sorption. The solvent phase from the extraction will contain in addition to the alcohol or diol water and oxygenates. The alcohol or diol can be separated for recycle, e.g., by stripping or fractionation of the solvent phase. The oxygenates pass with the water during such separations.

Typically oxygenates are removed from the feedstock prior to dehydrogenation. Since many dehydrogenation processes can tolerate the presence of water and many types of oxygenates such as alcohols, aldehydes, ketones and carboxylic acids that convert to water under dehydrogenation conditions, the dehydrogenation may alternatively be conducted prior to the removal of oxygenates.

Dehydrogenation is conducted in the presence of hydrogen and dehydrogenation catalyst under dehydrogenation conditions including elevated temperature. Any suitable dehydrogenation system may be used. In general, dehydrogenation conditions are selected to minimize cracking and polyolefin by-products. It is expected that typical dehydrogenation conditions will not result in any appreciable skeletal isomerization of the hydrocarbons in the dehydrogenation reactor. Dehydrogenation conditions include a temperature of generally from about 400° C. (752° F.) to about 900° C. (1652° F.) and preferably from about 420° C. (788° F.) to about 550° C. (1022° F.), a pressure of generally from about 1 kPa(g) (0.15 psi(g)) to about 1000 kPa(g) (145 psi(g)), and a LHSV of from about 0.1 to about 100 $hr^{-1}$. As used herein, the abbreviation "LHSV" means liquid hourly space velocity, which is defined as the volumetric flow rate of liquid per hour divided by the catalyst volume, where the liquid volume and the catalyst volume are in the same volumetric units. Generally for normal paraffins, the lower the molecular weight the higher the temperature required for comparable conversion. The pressure in the dehydrogenation zone is maintained as low as practicable, usually less than 350 kPa(g) (50.8 psi(g)) to maximize chemical equilibrium advantages.

The feedstock containing $C_5$ and $C_6$ paraffins may be admixed with a diluent material before, while, or after passing to the dehydrogenation zone. The diluent material may be hydrogen, steam, methane, ethane, carbon dioxide, nitrogen, argon, and the like, or a mixture thereof. Hydrogen is the preferred diluent. Ordinarily, when hydrogen is utilized as the diluent it is utilized in amounts sufficient to ensure a hydrogen to hydrocarbon mole ratio of about 0.1:1 to about 40:1, with best results being obtained when the mole ratio range is about 1:1 to about 10:1. The diluent hydrogen stream passed to the dehydrogenation zone will typically be recycled hydrogen separated from the effluent from the dehydrogenation zone in the hydrogen separation zone.

Water or a material which decomposes at dehydrogenation conditions to form water such as an alcohol, aldehyde, ether, or ketone, for example, may be added to the dehydrogenation zone, either continuously or intermittently, in an amount to provide, calculated on the basis of equivalent water, about 1 to about 20,000, preferably about 1 to about 10,000, mass-ppm of the hydrocarbon feed stream.

Any suitable dehydrogenation catalysts can be used. The choice of a particular dehydrogenation catalyst is not critical to this embodiment. Typically the catalyst comprises at least one platinum group (Groups 8-10 of the periodic table) metal and at least one promoter metal on a suitable support, usually a refractory oxide such as alpha alumina, theta alumina, cordierite, zirconia, titania, and mixtures thereof. Platinum group metals include platinum, palladium, rhodium, iridium, ruthenium, and osmium. Promoter metals typically are selected from the group consisting of tin, germanium, rhenium, gallium, bismuth, lead, indium, cerium, silver, zinc, and mixtures thereof, while modifier metals are selected from the group consisting of alkali metals, alkaline earth metals such as lithium, sodium, potassium, cesium, rubidium, beryllium, magnesium, calcium, strontium, barium, and mixtures thereof. The concentration of each metal component can vary substantially. The platinum group metal is often present in a concentration of about 0.01 to about 5 mass-percent on an elemental basis of the entire mass of the catalyst. The promoter metal may be present in an amount from about 0.05 to about 5 mass-percent while the modifier metal may be present in an amount from about 0.1 to about 5 mass-percent. The atomic ratio of the platinum group metal to promoter metal typically falls within the range of from about 0.05 to about 5. See, for instance, U.S. Pat. Nos. 3,274,287; 3,315,007; 3,315,008; 3,745,112; 4,430,517; 4,716,143; 4,762,960; 4,786,625; and 4,827,072.

The dehydrogenation catalyst may be in a fixed bed or a moving catalyst bed or a fluidized bed. The dehydrogenation zone may comprise one or more catalyst-containing reaction zones with heat exchangers there between to ensure that the desired reaction temperature is maintained at the entrance to each reaction zone. One or more hot hydrogen-rich gas streams may be introduced between a first and a second reaction zone to increase the temperature of a stream passing from the first to the second reaction zone.

Each reaction zone may be operated in a continuous-type or batch-type manner. Each reaction zone may contain one or more catalyst beds. Hydrocarbons may contact any catalyst bed in an upward-, downward-, or radial-flow fashion. In a particularly compact and efficient arrangement, the contacting of the catalyst with hydrocarbons and heat exchanging may be accomplished in a heat exchanging reactor.

The dehydrogenated product is typically a mixture of unreacted paraffins and olefins. The conversion of paraffins to olefins is equilibrium limited. Normally, the conversion of paraffins to olefins is between about 5 and 40, preferably between about 7 and 30, mole percent. With limited conversion of paraffins to olefins, it may be possible to generate little dienes. See, for instance, US 2004/0176655 where a low conversion per pass dehydrogenation unit operation is used to avoid generation of deleterious amounts of dienes.

In the preferred aspects of the process embodiments, however, the dehydrogenation conditions are sufficiently severe that higher conversions of paraffins to olefins are obtained, e.g., from about 10 to 35, mole percent even though these conditions result in diene being co-produced. Typically under these more severe conditions, the diene is present in an amount of at least about 1, say, about 3 to 25, mass-percent based upon the mass of the total olefin (mono- and di-olefin) in the dehydrogenated product. Also, in this preferred embodiment, cyclics are formed. As the feedstock generally contains little $C_7$ and higher hydrocarbons, the cyclics are rich in benzene. Normally, of the cyclics, benzene constitutes at least about 40, say, between about 40 and 95, mass-percent of the cyclics. The conversion of paraffins to cyclics is often in an amount between about 1 and 10, say, about 5 and 20, mass-percent of the paraffins fed to the dehydrogenation. In one embodiment, the concentration of cyclics or aromatic compounds in the dehydrogenated product is at least 5 mass-percent. The concentration of cyclics or aromatic compounds in the dehydrogenated product is often between about 1 and 10, say, about 5 and 20 mass-percent. The concentration of cyclics in the dehydrogenated product may be greater as unreacted hydrocarbons may be recycled to the dehydrogenation step and cyclics can build-up in the recycle stream.

The dehydrogenated product is the feed for synthesizing detergent range olefins. Especially where the dehydrogenation has been conducted to achieve higher conversions of paraffins, and thus contains diene, the dehydrogenated product is subjected to selective hydrogenation. If the dehydrogenation is under low conversion per pass conditions, it may be acceptable only to subject the detergent olefin-containing product stream to selective hydrogenation.

In broad terms, regardless of whether the dehydrogenated product or the detergent olefin-containing product stream is subjected to selective hydrogenation, the stream to be selectively hydrogenated is contacted with selective hydrogenation catalyst under selective hydrogenation conditions including the presence of hydrogen and elevated temperature. Selective hydrogenation processes are normally performed at relatively mild hydrogenation conditions. A broad range of suitable operating pressures therefore extends from about 40 kPa(g) (5.8 psi(g)) to about 250 kPa(g) (36.3 psi(g)) to 6000 kPa(g) (870 psi(g)), preferably between about 300 kPa(g) (43.5 psi(g)) and 2000 kPa (g) (290 psi(g)). A relatively moderate temperature between about 25° C. (77° F.) to about 350° C. (682° F.), preferably 50° C. (122° F.) to 200° C. (392° F.), is often used. The mole ratio of hydrogen to diolefinic hydrocarbons to achieve a certain conversion is dependent upon both reactor temperature and the molecular weight of the feed hydrocarbons. To avoid the undesired saturation of a significant amount mono-olefinic hydrocarbons, there should be less than 2.0 times the stoichiometric amount of hydrogen required for the selective hydrogenation of the diolefinic hydrocarbons which are present in the liquid phase process stream to mono-olefinic hydrocarbons. Preferably, the mole ratio of hydrogen to diolefinic hydrocarbons in the material entering the bed of selective hydrogenation catalyst is maintained between 0.75:1 and 1.8:1. The selective hydrogenation catalyst may be any suitable catalyst for effecting mild hydrogenation, and are usually supported hydrogenation metal such as nickel (especially sulfided nickel), platinum or palladium. See, for instance, U.S. Pat. Nos. 3,234,298; 3,472,763; 3,662,015; 4,695,560 and 5,276,231, all of which are herein incorporated in their entireties by reference. The liquid hourly space velocity of the reactants through the selective hydrogenation catalyst should be above 1.0 $hr^{-1}$. Preferably, it is above 5 $hr^{-1}$, and more preferably it is between 5 and 35 $hr^{-1}$. In preferred aspects, the selective hydrogenation conditions are sufficient to reduce the diene concentration to less than about 0.5, preferably less than about 0.3, mass-percent dienes based upon the total mass of olefins in the selective hydrogenation effluent.

Where the selective hydrogenation follows the chain growth reaction to form the detergent range olefins, the dehydrogenation is preferably conducted to minimize the formation of dienes. Typically, the detergent range olefins would be separated from the lower boiling hydrocarbons and this separated stream would be subjected to the dehydrogenation conditions. This detergent range olefin-containing would contain similar carbon atom-containing dienes, but, because of the less severe dehydrogenation conditions employed, in a relatively small amount, e.g., less than about 1, preferably less than about 0.5, mass-percent based upon the total olefins.

Alternatively, especially where the feedstock containing $C_5$ and $C_6$ paraffins also contains olefins and, prior to dehydrogenation, is subjected to chain growth reaction conditions to form a detergent range olefin product comprising $C_{10}$ to $C_{12}$ mono-olefins, the feedstock may be selectively hydrogenated. In this embodiment, the feedstock is preferably admixed with the recycling lower boiling fraction of paraffins and unreacted olefins from the reaction to form the detergent range olefin product. This admixture is subjected to the selective hydrogenation to reduce the presence of any dienes that may be in the feedstock.

The selective hydrogenation catalyst may be in a fixed bed or a moving catalyst bed or a fluidized bed. The selective hydrogenation zone may comprise one or more catalyst-containing reaction zones with heat exchangers there between to ensure that the desired reaction temperature is maintained at the entrance to each reaction zone. One or more hydrogen-rich gas streams may be introduced between a first and a second reaction zone to increase the temperature of a stream passing from the first to the second reaction zone.

Each reaction zone may be operated in a continuous-type or batch-type manner. Each reaction zone may contain one or more catalyst beds. Hydrocarbons may contact any catalyst bed in an upward-, downward-, or radial-flow fashion. In a particularly compact and efficient arrangement, the contacting of the catalyst with hydrocarbons and heat exchanging may be accomplished in a heat exchanging reactor.

The dehydrogenated product which contains $C_5$ and $C_6$ olefins is subjected to chain growth reaction conditions sufficient to provide a detergent range olefin product comprising $C_{10}$ to $C_{12}$ mono-olefins (herein referred to as the "chain growth reaction"). The particular type of chain growth reaction is not critical to the broadest aspects of the process embodiments. The chain growth reaction may be one or more of dimerization and metathesis, which may be in combination with oligomerization.

Dimerization conditions typically include the presence of a catalyst and the use of elevated temperature and pressures. The specific temperature and pressure conditions used will depend, in part, upon the type of catalyst employed. A wide variety of catalysts have been proposed including homogeneous and heterogeneous catalysts. Examples of homogeneous catalysts include hydrogen fluoride, boron trifluoride and trifluoroacetic acid. Heterogeneous catalysts include suitable silica-aluminas, sulfated zirconias and molecular sieves and supported metal-containing catalysts that often contain at least one element selected from Groups 3, 4, 8 to 10, and 14 of the periodic table. References herein to the periodic table are to the new IUPAC notation as shown on the Periodic Table of the Elements in the inside front cover of the CRC Handbook of Chemistry and Physics, 80th Edition, 1999-2000, CRC Press, Boca Raton, Fla., USA. The metal element is usually in combined form such as an oxide, sulfide or oxysulfide. Due to selectivity to dimerization, catalysts containing nickel oxide or iron oxide are most frequently used. Suitable supports include silica, alumina, silica-aluminas including molecular sieves. See, for instance, U.S. Pat. Nos. 5,169,824 and 5,849,972. Temperatures for the dimerization are generally in the range of about 40° C. (104° F.) to 250° C. (482° F.), preferably about 60° C. (140° F.) to 200° C. (392° F.), and pressures may be within range of 100 kPa(a) (14.5 psi(a)) to 2000 kPa(a) (290 psi(a)), say, 110 kPa(a) (16 psi(a)) to 1000 kPa(a) (145 psi(a)).

Heterogeneous dimerization catalyst may be in a fixed bed or a moving catalyst bed or a fluidized bed. The dimerization zone may comprise one or more catalyst-containing reaction zones with heat exchangers there between to ensure that the desired reaction temperature is maintained at the entrance to each reaction zone. Preferably more than one reaction zone is used with intervening fractionation to remove dimerized product. Each reaction zone may be operated in a continuous-type or batch-type manner. Each reaction zone may contain one or more catalyst beds. Hydrocarbons may contact any catalyst bed in an upward-, downward-, or radial-flow fashion.

Preferably the dimerization conditions are such that on a per pass basis at least about 20, more preferably about 30 to 70, mass-percent of the olefin is converted to dimers and highers with at least about 70, preferably at least about 75, mass-percent of the conversion being to dimers. Preferably little, if any, $C_{10}$ to $C_{12}$ paraffins are formed during the dimerization, and often the dimerization product contains less than about 0.1, preferably less than about 0.01, mass-percent $C_{10}$ to $C_{12}$ paraffins.

Metathesis reaction conditions include the presence of a metathesis catalyst. The catalyst may be homogeneous or heterogeneous. Catalytically-active elements proposed for metathesis catalysts include elements from Groups 4, 5, 6, 7, and 8 to 10 of the periodic table, including one or more of titanium, niobium, tantalum, molybdenum, tungsten, rhenium, ruthenium, osmium and iridium, especially one or more of rhenium, tungsten and molybdenum. The ultimate form of the catalytically active component may be an oxide, sulfide or oxysulfide or in a ligand structure. The heterogeneous catalysts are generally supported, for instance, on a refractory oxide support or a molecular sieve-containing support. See, for instance, Chapter 2 of "Olefin Metathesis and Metathesis Polymerization" by K. J. Ivin and J. C. Mol, Academic Press, San Diego, Calif., USA (1997). Temperatures for the metathesis are generally in the range of about 20° C. (68° F.) to 300° C. (572° F.), preferably about 35° C. (95° F.) to 150° C. (302° F.), and pressures may be within range of 100 kPa(a) (14.5 psi(a)) to 2000 kPa(a) (290 psi(a)), say, 110 kPa(a) (16 psi(a)) to 1000 kPa(a) (145 psi(a)).

The heterogeneous metathesis catalyst may be in a fixed bed or a moving catalyst bed or a fluidized bed. The metathesis zone may comprise one or more catalyst-containing reaction zones. Each reaction zone may be operated in a continuous-type or batch-type manner. Each reaction zone may contain one or more catalyst beds. Hydrocarbons may contact any catalyst bed in an upward-, downward-, or radial-flow fashion. Each zone may have associated with it a fractionation column to recover and recycle lower molecular weight olefin and remove detergent range olefin product.

Preferably the metathesis conditions are such that at least about 30, more preferably about 40 to 95, mass-percent of the olefin is converted to detergent range olefins. Preferably little, if any, $C_{10}$ to $C_{12}$ paraffins are formed during the metathesis, and often the metathesis product contains less than about 0.1, preferably less than about 0.01, mass-percent $C_{10}$ to $C_{12}$ paraffins.

The by-products of metathesis are ethylene and propylene that have value, especially in an integrated refinery and alkylbenzene production facility.

Oligomerization can be used where the $C_5$-$C_6$ feedstock also contains a significant amount of $C_4$ hydrocarbons or in combination with a metathesis chain growth operation to convert lower olefins to detergent range olefins or to $C_5$ and $C_6$ olefins for metathesis or dimerization. Oligomerization conditions typically include the presence of a catalyst and the use of elevated temperature and pressures. The specific temperature and pressure conditions used will depend, in part, upon the type of catalyst employed. A wide variety of catalysts have been proposed including homogeneous and heterogeneous catalysts. Examples of homogeneous catalysts include hydrogen fluoride, boron trifluoride and trifluoroacetic acid. Homogeneous catalysts also include metal coordination catalysts such as Ziegler-Natta and metallocene-type catalysts. Heterogeneous catalysts include suitable silica-aluminas, sulfated zirconias and molecular sieves and supported metal-containing catalysts. The metals for the homogeneous and heterogeneous catalysts often comprise at least one element selected from Groups 3, 4, 14, and 8 to 10 of the periodic table. The element is usually in combined form such as an oxide, sulfide or oxysulfide or in a ligand structure. Catalysts containing nickel, cobalt or iron, usually as oxides, are most frequently used. Suitable supports include silica, alumina, silica-aluminas including molecular sieves. See, for instance, U.S. Pat. Nos. 5,169,824 and 5,849,972. Temperatures for the oligomerization are generally in the range of about 100° C. (212° F.) to 250° C. (482° F.), preferably about 120° C. (248° F.) to 200° C. (392° F.), and pressures may be within range of 100 kPa(a) (14.5 psi(a)) to 2000 kPa(a) (290 psi(a)), say, 110 kPa(a) (16 psi(a)) to 1000 kPa(a) (145 psi(a)).

The heterogeneous oligomerization catalyst may be in a fixed bed or a moving catalyst bed or a fluidized bed. The oligomerization zone may comprise one or more catalyst-containing reaction zones with heat exchangers there between to ensure that the desired reaction temperature is maintained at the entrance to each reaction zone. Preferably more than one reaction zone is used with intervening fractionation to remove oligomerized product. Each reaction zone may be operated in a continuous-type or batch-type manner. Each reaction zone may contain one or more catalyst beds. Hydrocarbons may contact any catalyst bed in an upward-, downward-, or radial-flow fashion.

Preferably the oligomerization conditions are such that on a per pass basis at least about 20, more preferably about 30 to 70, mass-percent of the olefin is converted to dimers and highers with at least about 60, preferably at least about 70, mass-percent of the conversion being to detergent range olefins. Preferably little, if any, $C_{10}$ to $C_{12}$ paraffins are formed during the oligomerization, and often the product contains less than about 0.1, preferably less than about 0.01, mass-percent $C_{10}$ to $C_{12}$ paraffins.

In preferred embodiments, a detergent range olefin fraction is separated, usually by distillation, from the effluent from the chain growth reaction. A lower molecular weight fraction, e.g., having $C_4$-$C_7$ hydrocarbons, can be recycled to the dehydrogenation step. As the dehydrogenated product contains significant amounts of $C_5$ and $C_6$ paraffins due to the equilibrium limitation on conversion, a recycle provides for efficient utilization of feedstock. Normally, this recycle stream will contain from about 40 to 98 mass-percent paraffins, less than 5 mass-percent olefins, and, depending upon the co-production of cyclics during the dehydrogenation and the volume of the cyclics removed from the reaction loop discussed below, from about 0.1 to 60, mass-percent cyclics.

To prevent an undue build-up of cyclics (i.e., above 60 mass-percent) in a reaction loop with the dehydrogenation and the chain growth reaction, a cyclics-containing stream is typically removed. The removal may be effected by subjecting all or a portion of the fluid in the reaction loop to a separation process to remove cyclics. While distillation can be used, membrane separation, extraction and sorption techniques are generally preferred for selective removal of cyclics, especially aromatics. In a preferred aspect of the process embodiments, a slip stream, or purge, is taken from the loop, preferably downstream from the chain growth reaction.

Benzene is a primary constituent of the cyclics and is a raw material for making alkylbenzenes. Where the dehydrogenation is operated to form aromatics, preferably at least a portion of the benzene is recovered and used as a portion of the benzene feed for the alkylation step. Because the process embodiments use a feed primarily containing $C_5$ and $C_6$ paraffins, the formation of higher, less desirable aromatics such as toluene, is much less than that occurring with the dehydrogenation of a $C_{10}$ to $C_{12}$ paraffin-containing stream.

In one embodiment, at least a portion of the purge is subjected to dealkylation conditions to convert any toluene and higher aromatics to benzene. If the dealkylation is done under hydrocracking conditions, the dealkylation conditions may also hydrogenate any olefins present. The benzene can be separated from the dealkylation effluent or the dealkylation effluent can be fed to the alkylation reaction, and the non-aromatics in admixture with the benzene can serve as a heat sink to assist in removal of heat from the exothermic alkylation reaction. Alternatively, at least a portion of the non-aromatics can be separated and, if desired, recycled to the dehydrogenation.

Suitable dealkylation processes for benzene-forming include hydrodealkylation, steam dealkylation, oxidative dealkylation in combination with steam or among others. Hydrodealkylation can be thermal and or catalytic. Thermal hydrodealkylation is preferred. The benzene-forming conditions are preferably sufficient to dealkylate at least about 70, more preferably at least about 85, and sometimes between about 85 and 98, mass-percent of the aromatic by-products.

In general, hydrodealkylation conditions include elevated temperatures and pressures, e.g., about 200° C. (392° F.) to 700° C. (1292° F.) and 100 kPa(g) (14.5 psi(g)) to 5000 kPa(g) (725 psi(g)) and the presence of hydrogen, e.g., from about 1:1 to 50:1 moles of hydrogen per mole of aromatic by-products. Thermal hydrodealkylation is typically at temperatures of between about 500° C. (932° F.) or 575° C. (1067° F.) and 700° C. (1291° F.). Often the pressures of thermal hydrodealkylation are in the range of about 2500 kPa(g) (363 psi(g)) to 3500 kPa(g) (508 psi(g)). Exemplary thermal hydrodealkylation conditions are described in, for instance, W. L. Liggin, UOP Thermal Hydrodealkylation (THDA) Process, in Handbook of Petroleum Refining Processes, Second Edition (1997), at pp. 2.23 to 2.26.

Catalytic hydrodealkylation conditions are generally milder than those used for thermal hydrodealkylation. Temperatures of about 200° C. (392° F.) to 600° C. (1112° F.), say, 250° C. (482° F.) to 550° C. (1022° F.), are often employed. Pressures are generally in the range of about 100 kPa(g) (14.5 psi(g)) to 3500 kPa(g) (508 psi(g)). Often, the milder catalytic hydrodealkylation conditions will result in less cracking of the alkyl groups removed from the aromatic by-products, that is, light ends may contain a lesser concentration of methane than would occur from a thermal hydrodealkylation. Hence, less hydrogen may be required, e.g., from about 1 to 10 moles of hydrogen per mole of aromatic by-products. Any suitable hydrodealkylation catalyst may be used. Typical catalysts are acidic catalysts including aluminas, silicas, silica aluminas such as zeolites including dealuminated Y, silicalite, zeolites having the MOR framework type, zeolite beta, ZSM-5, zeolites having the MTW framework type, UZM-4, UZM-5, UZM-8, UZM-16; silica aluminophosphates such as SAPO-34, SAPO-11, SAPO-31, SAPO-5, SAPO-18, and MAPSO-43; which may be supported or unsupported. References herein to zeolite framework types are to those in the Atlas of Zeolite Framework Types, Fifth Revised Edition, 2001, Elsevier, New York, USA. UZM-4 is described in U.S. Pat. No. 6,419,895, herein incorporated by reference in its entirety. UZM-5 and UZM-6 are described in U.S. Pat. Nos. 6,613,302 and 6,388,157, which are herein incorporated in their entireties by reference. UZM-8 is described in U.S. Pat. No. 6,756,030, herein incorporated by reference in its entirety. UZM-16 is described in U.S. Pat. No. 6,752,980, herein incorporated by reference in its entirety. In some instances, the catalyst is halogenated, e.g., fluorided or chlorided, to enhance acidity. The catalyst may also comprise one or more adjuvants or agents which may serve as catalysts, promoters and activity modifiers. Active metals can be from Groups 4, 5, 6, 7, and 8 to 10 of the periodic table, such as platinum and rhenium. Promoters and/or activity modifiers can be selected from Groups 1, 2, 13, 14, 15, and 16 of the periodic table, such as tin, lead, germanium, and sulfur.

As the benzene-forming conditions typically involve the presence of hydrogen, preferred process embodiments recover unreacted hydrogen from the product of the benzene-forming conditions for recycle. Generally this recovery is done by gas/liquid phase separation.

A benzene product stream is generated as a result of subjecting the cyclics-containing stream to benzene-forming conditions. This benzene product stream will contain benzene and non-aromatics including non-aromatics fed to the dealkylation and conversion products of the dealkylation. Lights such as methane, ethane, propane, and the like that have been removed from the phenyl ring can be removed from the benzene in the benzene product stream by distillation, including flash distillation, or by liquid gas separation where the conditions of the product stream are not adequate to maintain the lights in the liquid stream.

The detergent range olefin-containing fraction, if the dehydrogenated product has not already been subjected to selective hydrogenation, is selectively hydrogenated and is used for the alkylation of benzene.

Various processes have been proposed for the alkylation of benzene. See, for instance, Peter R. Pujado, Linear Alkylbenzene (LAB) Manufacture, in Handbook of Petroleum Refining Processes, Second Edition (1997), at pp. 1.53 to 1.66. The most common processes are those involving the presence of hydrogen fluoride ("HF Processes") and those involving the use of a solid acidic catalyst ("Solid Catalyst Processes"). In general, the HF Process and the Solid Catalyst Process involve contacting an olefin with a stoichiometric excess of benzene at elevated temperature to produce alkylbenzene.

The amount of benzene present during the alkylation will depend upon the sought conversion selectivity to alkylbenzene. In general, the greater the stoichiometric excess of benzene, the greater the selectivity to alkylbenzene. Typically, the mole ratio of benzene to olefin during alkylation is within the range of about 5:1 to 50:1 or more. For the HF Processes, this ratio is often between about 5:1 to 10:1, and for the Solid Catalyst Processes, between about 10:1 to 30:1. The olefin-containing feed to the alkylation reactor should be sufficiently free of impurities, such as water and sulfur compounds that can unduly adversely affect the life of the alkylation catalyst.

U.S. Pat. No. 4,463,205, herein incorporated by reference in its entirety, discloses typical HF Processes. In these HF Processes, the reactants are normally subjected to vigorous mixing and agitation at the point of initial contact of the olefin and the liquid-phase hydrogen fluoride. The alkylation zone preferably has an overall arrangement similar to that shown in U.S. Pat. No. 3,494,971. In this arrangement, the two feed hydrocarbons and liquid phase HF are charged to a reactor. The effluent of this reactor is passed into a first settling zone and separated into HF and hydrocarbon phases. The HF is withdrawn and divided into a portion passed into a regenerator and a portion returned to the reactor. A hydrocarbon phase is withdrawn from the first settling zone and charged to a contactor, which is sometimes referred to as a second "reactor" as the only hydrocarbon charged to the contactor. The HF charged to the contactor is a mixture of newly regenerated HF and HF withdrawn from a second settling zone, which receives the total effluent of the contactor. A portion of the HF withdrawn from the second settling zone is charged to the reactor to replace the HF withdrawn for regeneration. The hydrocarbon phase which is withdrawn from the second settling zone may be withdrawn as the alkylation zone effluent stream but is preferably passed into a stripping column in which dissolved HF is removed overhead and some of the feed aromatic hydrocarbon is also recovered. The net bottoms stream of this HF stripping column becomes the alkylation zone effluent stream charged to the fractionation zone of the subject process.

The alkylation reaction zone is maintained at alkylation-promoting conditions. As used herein, the term "alkylation-promoting conditions" is intended to include a pressure sufficient to maintain the reactants and HF in a liquid phase. A general range of operating pressures is from about 200 kPa(a) (29.0 psi(a)) to 4500 kPa(a) (653 psi(a)). The temperature range covered by this set of conditions is from about −20° C. (−4° F.) to about 95° C. (203° F.), but the reaction is preferably conducted at a temperature of from 15° C. (59° F.) to 70° C. (158° F.). The volumetric ratio of HF to the total amount of hydrocarbons entering the reactor should be maintained within the broad range of from about 0.2:1 to about 10:1, preferably from 0.5:1 to 2:1.

The effluent streams leaving the reactor will typically be an intimate admixture of liquid phase hydrocarbons and liquid phase hydrogen fluoride. They may be in the form of a true emulsion. A considerable residence time is normally required to separate these two liquid phases, and the effluent streams are therefore passed into settling zones. The two settling zones will normally be maintained at a temperature that is set by the entering HF-hydrocarbon mixtures withdrawn from the respective upstream zones. They will therefore be at substantially the same temperature as the immediately upstream reactor or contactor. The same is also normally true for the pressures used in the settling zones after adjustment for any pressure change due to liquid flow and elevation differences. The settling zones may however be downstream of control valves and therefore operated at a somewhat reduced pressure. This reduced pressure, however, must be superatmospheric and sufficient to maintain liquid phase conditions. A residence time for both the acid and hydrocarbon phases in the settling zones should be in excess of 30 seconds but less than 30 minutes.

Regeneration of the HF catalyst is normally accomplished by stripping the acid under conditions sufficient to decompose alkylfluorides and to produce an overhead vapor stream containing HF and the stripping media. Benzene available within the process is a suitable stripping media. The overhead vapor stream of the column is passed into a condenser, the resultant condensate is allowed to separate into an acid phase and a benzene phase containing dissolved HF.

The overhead vapor stream of the HF regeneration column will contain vapor-phase HF and the benzene. This vapor stream has a low concentration of the higher boiling impurities. The higher boiling materials are concentrated into a relatively small stream removed from the HF regeneration column as a net bottoms stream. The benzene present in the overhead vapor stream of the HF regeneration column is derived mainly from the reflux liquid fed to the top of this column. A small amount of benzene is also dissolved in the liquid phase HF stream fed to HF regeneration column. The reflux liquid is preferably removed from the overhead receiver, which collects the condensed overhead of the HF stripping column. It is not necessary to supply reflux liquid for successful operation of the HF regeneration column if the feed stream is passed into the top of the column.

The hydrocarbonaceous phase removed from the second settling zone is preferably passed into a stripping column referred to as the HF stripping column. The function of this column is to prevent the passage of HF into the downstream fractionation zone. Representative conditions for the operation of the HF stripping column include an overhead vapor temperature of about 100° C. (212° F.) to 125° C. (257° F.) at a pressure of about 200 kPa(g) (29.0 psi(g)) to 300 kPa(g) (43.5 psi(g)). There is normally no external reflux to this column. The overhead vapor stream of the HF stripping column is normally condensed by cooling it to about 35° C. (95° F.) or less.

In the Solid Catalyst Processes, benzene and the olefin are reacted under alkylation conditions in the presence of a solid alkylation catalyst. These alkylation conditions generally include a temperature in the range between about 80° C. (176° F.) and about 200° C. (392° F.), most usually at a temperature not exceeding about 175° C. (347° F.). Since the alkylation is typically conducted in at least partial liquid phase, and preferably in either an all-liquid phase or at supercritical conditions, pressures must be sufficient to maintain reactants in the desired phase. The requisite pressure necessarily depends upon the olefin and temperature, but normally is in the range of about 1300 kPa(g) (189 psi(g)) to 7000 kPa(g) (1015 psi(g)), and most usually between about 2000 kPa(g) (290 psi(g)) and 3500 kPa(g) (508 psi(g)).

Alkylation of benzene by the olefins is conducted in a continuous manner, and one or more catalyst beds in flow series are used. For purposes herein, a catalyst bed is termed a reactor whether in the same or a separate vessel from another bed. In preferred process embodiments 2 or 3 reactors can be used to achieve an advantageous combination of performance and capital expense avoidance.

The catalyst may be used as a packed bed or a fluidized bed. The feed to the reaction zone may be passed either upflow or downflow, or even horizontally as in a radial bed reactor. In one desirable variant, olefin-containing feedstock may be fed into several discrete points within the reaction zone, and at each zone the benzene to olefin mole ratio may be greater than 50:1. The total feed mixture, that is, aromatic compound plus olefin, is often passed through the packed bed at a liquid hourly space velocity (LHSV) between about 0.3 and about 6 $hr^{-1}$ depending upon, e.g., alkylation temperature and the activity of the catalyst. Lower values of LHSV within this range are preferred.

Any suitable alkylation catalyst may be used in the process embodiments, provided that the requirements for conversion, selectivity, and activity are met. U.S. Pat. Nos. 5,196,574 and 5,344,997 describe alkylation of aromatics using a fluorided silica-alumina catalyst. U.S. Pat. No. 5,302,732 describes alkylation of aromatics using an ultra-low sodium silica-alumina catalyst. The teachings of U.S. Pat. Nos. 5,196,574, 5,302,732, and 5,344,997 are incorporated herein by reference. Preferred alkylation catalysts comprise zeolites having a zeolite framework type selected from the group consisting of FAU, BEA, MOR, MTW, MWW and NES. Preferred zeolites include mordenite, ZSM-4, ZSM-12, ZSM-20, offretite, gmelinite, beta, NU-87, and gottardiite. Further discussion of alkylation catalysts can be found in U.S. Pat. Nos. 6,315,964 and 6,617,481.

In the preferred embodiments, the alkylation conditions regardless of whether the HF Process or Solid Catalyst Processes are used, are such that the alkylation effluent contains less than about 1000, preferably less than about 100, ppm-mass of unreacted olefin.

As mentioned above, the alkylation reaction is exothermic. One method for assisting in the abatement of any exotherm is to feed a relatively dilute olefin-containing stream to the alkylation. Benzene, by being supplied in a greater than stoichiometric amount, serves as a heat sink as well as kinetically driving the reaction to the mono-alkylbenzenes. Where the detergent range olefin has been derived by dehydrogenating a paraffin of similar carbon number, the olefin-containing feed to the alkylation is about 85 to 90 mass-percent paraffin. In certain of the preferred embodiments, the detergent olefin fed to the alkylation step has little, if any paraffin. In such event, the benzene to olefin ratio may be increased to provide the desired heat sink. Alternatively, a stream containing $C_5$ and $C_6$ paraffins which is essentially devoid of olefins may be supplied to the alkylation in an amount sufficient to provide the sought heat sink. Often, the mole ratio of the $C_5$ and $C_6$ paraffins in this stream to the detergent range olefins in the feed to the alkylation is between about 1:1 to 20:1.

The paraffins, having a similar boiling point to benzene, can be recovered from the alkylation effluent with the benzene and recycled with the benzene. To prevent build-up of these paraffins, a purge may be taken from the benzene loop. The purge may be used for fuel value but preferably the hydrocarbon values are recovered. For instance, benzene may be recovered from the purge by extraction, membrane separation or sorption. At least a portion of the recovered benzene may be returned to the alkylation. At least a portion of the paraffin-containing fraction from the separation may be returned to the dehydrogenation zone. Alternatively, at least a portion of the purge without separation of benzene may be returned to the dehydrogenation step. The benzene can then be recovered from a purge from the dehydrogenation-chain grown reaction loop as discussed above.

The alkylation reactor effluent is passed to a distillation assembly that separates benzene for recycle. If significant amounts of paraffins in the $C_8$ and higher range are present, it may also be necessary to provide a further distillation to separate as the overhead, paraffins, and the bottoms from this second distillation assembly would be fed to a heavies distillation assembly where the alkylbenzene product is contained in the overhead. If desired, a finishing column may be used to further purify the alkylbenzene, especially after a clay treatment to remove color precursors. In this type of distillation train, the bottoms stream for the lights distillation is normally fed to the distillation assembly for separating the benzene. If the alkylation effluent contains unreacted olefin, then the use of the second distillation assembly is preferred to remove the olefin.

Typically the benzene distillation is generally conducted with a bottoms temperature of less than about 300° C. (572° F.), preferably less than about 275° C. (527° F.), usually between about 230° C. (446° F.) and 270° C. (518° F.), and at a pressure at which the overhead is provided of between about 5 kPa(g) (0.7 psi(g)) and 300 kPa(g) (43.5 psi(g)), preferably between about 35 kPa(g) (5.1 psi(g)) and 70 kPa(g) (10.2 psi(g)). Where a lower carbon number paraffin is present, e.g., as a heat sink, the paraffin may also be contained in the benzene overhead. Generally, the distillation assembly is operated to assure that the bottoms stream contains virtually no benzene. Preferred processes provide additional advantages with respect to the benzene column. First, where the feed to the alkylation is substantially devoid of $C_8$ and higher paraffins, the separation can be effected with fewer distillation plates and less reboiler energy consumption than a conventional alkylbenzene process where benzene must be separated from paraffins corresponding in carbon number to the detergent range olefins. Second, since the aromatics that are co-produced with the olefins in the dehydrogenation can be readily separated from the detergent range olefin by distillation, the need for a sorption to remove aromatics from the detergent range olefins is obviated. As the sorption uses highly pure benzene for regeneration, the need for such highly pure benzene is obviated. Thus additional capital and operating costs in the refining of the alkylbenzene can be avoided.

The benzene distillation assembly may comprise one or more distillation columns. More than one overhead may be obtained from the benzene distillation assembly. Each column may contain any convenient packing or distillation trays, but most often trays such as sieve and bubble trays, are used. Often the assembly provides at least about 3, say 5 to 70, and preferably 5 to 10, theoretical plates. The reflux ratio (herein defined as the distillate to reflux mass ratio) is often in the range of about 2:1 to 1:10, preferably about 1.5:1 to 1:5. The bottoms stream from the benzene distillation generally contains less than about 1000 parts by million by mass (mppm), preferably less than about 50 mppm, and sometimes less than about 5 mppm, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

If necessary, a paraffin distillation is conducted. The paraffins distillation typically involves a bottoms temperature of less than about 300° C. (572° F.), preferably less than about 275° C. (527° F.), usually between about 250° C. (482° F.) and 275° C. (527° F.), and a pressure at which overhead is provided of between about 5 kPa(a) (0.7 psi(a)) and 110 kPa(a) (16 psi(a)), preferably between about 10 kPa(a) (1.5 psi(a)) and 50 kPa(a) (7.3 psi(a)). The column may contain any convenient packing or distillation trays, but most often sieve trays are used. Often the paraffins distillation assembly provides at least about 5, say 7 to 20, theoretical plates. The reflux ratio is often in the range of about 3:1 to 1:10, preferably about 1:1 to 1:3. The bottoms stream from the paraffins distillation generally contains less than about 5000, preferably less than about 500, mppm paraffins and preferably less than about 10, often less than about 1, mppm benzene. The overhead from the paraffins column generally contains less than about 1, preferably less than about 0.5, and most preferably less than about 0.2, mass-percent alkylbenzene. The paraffins distillation may occur in a single column or two or more distinct columns may be used.

In the preferred aspects of this embodiment, no paraffins distillation is necessary and the bottoms from the benzene distillation assembly is directly provided to the heavy alkylate distillation.

The heavy alkylate distillation is generally conducted with a bottoms temperature of less than about 300° C. (572° F.), preferably less than about 275° C. (527° F.), usually between about 250° C. (482° F.) and 275° C. (527° F.), and at a pressure of between about 0.5 kPa(a) (0.07 psi(a)) and 30 kPa(a) (4.4 psi(a)), preferably between about 1 kPa(a) (0.14 psi(a)) and 5 kPa(a) (0.7 psi(a)). The column may contain any convenient packing or distillation trays, but most often structured packing is used. Often the heavy alkylate distillation assembly provides at least about 5, say 10 to 30, and preferably 10 to 20, theoretical plates. The reflux ratio is often in the range of about 2:1 to 1:5, preferably about 0.2:1 to 1:1. The overhead from the heavy alkylate distillation generally contains less than about 1000 mppm, preferably less than about 100 mppm, and sometimes less than about 50 mppm, total heavies.

The refining system may contain additional distillation zones, e.g., to recover additional alkylbenzene from heavies. At least a portion of the heavies-containing stream may be recycled to the dealkylation process for recovery of benzene.

Where an alkylbenzene stream contains olefinic components, the bottoms from the benzene distillation assembly or the overhead from the heavy alkylate distillation column can be subjected to a catalytic operation to reduce bromine index. In this catalytic operation, the alkylbenzene stream is passed to a catalytic conversion zone containing an acidic catalyst under olefin reduction conditions. The particular unit operation is not critical to the broad aspects of the process embodiments and any suitable operation may be used.

A number of processes for improving the quality of alkylbenzenes and reducing olefin content have been proposed. The catalysts may be clay or molecular sieve (natural or synthetic). Included in the clays are montmorillonite, laponite, saponite, and pillared clays. Filtrol F-24 (Engelhard Corporation, Iselin, N.J.) is a preferred clay. Molecular sieves include zeolites A, beta, L, S, T, X and Y and omega, mordenite, erionite, chabazite, boggsite, cloverite, gmelinite, offretite, pentasil molecular sieves having silica to alumina mole ratios greater than about 10, and silicoaluminophosphates (such as SAPO-5 and SAPO-41).

The olefin reduction is typically conducted at temperatures between about 25° C. (77° F.) and 250° C. (482° F.), and most often between about 70° C. (158° F.) and 150° C. (302° F.), under a pressure sufficient to maintain the alkylbenzene stream under liquid conditions, e.g., within the range of about 0.1 kPa(a) (0.01 psi(a)) to 150 kPa(a) (21.8 psi(a)). The contact time with the catalyst is sufficient to provide the desired reduction in bromine index. For a fixed bed system, the weight hourly space velocity is typically in the range of about 0.1 to 20 hr$^{-1}$. The bromine index of the treated alkylbenzene stream is preferably below about 10, more preferably below about 2. The olefin reduction conditions also cause byproducts such as the formation of dialkylbenzene and benzene from alkylbenzene and form oligomers and polymers from olefinic components.

The effluent from the olefin reduction is subjected to the fourth distillation to remove as an overhead, benzene, and heavies such as the dialkylbenzene and the oligomers and polymers from olefinic components.

With reference to FIG. 1, an apparatus is depicted that is capable of using dual feedstocks for making alkylbenzenes. In apparatus 100, a $C_5$-$C_6$-containing feedstock is provided via line 102 to oxygenate extractor 104. This feedstock may be obtained from any suitable source including a naphtha-range fraction or a Fischer-Tropsch process and thus usually contains normal paraffins. For purposes of this discussion, the feedstock contains olefins and oxygenates as well as some $C_5$-$C_6$ paraffins and some higher and some lower molecular weight paraffins and olefins. A methanol-water sorbent is introduced into extractor 104 via line 106 and the spent sorbent is withdrawn via line 108 for regeneration.

The $C_5$-$C_6$-containing feedstock having oxygenates removed is directed from extractor 104 to dimerization reactor 112 via line 110. While a dimerization reactor is shown, reactor 112 could also represent a metathesis reactor. A portion of the olefin in the $C_5$-$C_6$-containing feedstock is consumed to provide dimerized olefin primarily in the $C_{10}$ to $C_{12}$ range with some higher and some lower molecular weight olefins. The olefin will have some branching, but typically contains very little quaternary carbon branching. The presence of paraffins in the feedstock to the reactor advantageously serves as a heat sink to facilitate temperature control during the exothermic dimerization reaction. The feedstock now containing the dimer is passed from reactor 112 via line 114 to fractionation assembly 116 where lights such as hydrogen and cracking products are removed via line 120 and a stream containing $C_5$ and $C_6$ aliphatic hydrocarbons (paraffins and unreacted olefins) is withdrawn via line 122 and passed to dehydrogenation reactor 124 to convert a portion of the paraffins to the corresponding olefins. As the dehydrogenation is equilibrium affected, the product will contain olefins and paraffins. The dehydrogenation product is passed via line 126 to dimerization reactor 112 where in combination with the feedstock, the olefins are subjected to dimerization reaction conditions.

As discussed above, by directing the olefin-containing feedstock first to the dimerization reactor, enhanced efficiencies in the dehydrogenation and dimerization cycle loop are achieved since the feed to the dehydrogenation contains a lower concentration of olefin than does the $C_5$-$C_6$-containing feedstock.

The dimerized olefin is withdrawn from fractionation assembly 116 via line 128 and is introduced into selective hydrogenation reactor 130 where diolefins are converted to mono-olefins. Hydrogen required for the selective hydrogenation is supplied by line 131. The effluent from reactor 130 which contains olefins having a reduced concentration of dienes, is passed via line 132 to stripper 134 for removal of light ends contained in an overhead by line 136. Depending on the hydrogen and the $C_5$-$C_6$ contents of the overhead, the overhead may be recovered and recycled to the selective hydrogenation reactor or the $C_5$-$C_6$ dehydrogenation reactor.

Selective hydrogenation reactor 130 also treats a dehydrogenation product generated from a $C_{10}$-$C_{12}$ paraffin-containing feedstock supplied by line 138. This feedstock is dehydrogenated in dehydrogenation reactor 140 and the dehydrogenation effluent from reactor 140 is directed by line 142 to separator 144. The overhead from separator 144 is exhausted via line 146 and contains hydrogen. A portion of the overhead is recycled via line 148 to dehydrogenation reactor 140. The bottoms from separator 144 are passed via line 150 to selective hydrogenation reactor 130.

The bottoms from stripper 134 are passed via line 152 to sorption system 154 in which aromatics are selectively removed from the selective hydrogenation effluent. A suitable sorption system is described in, for instance, U.S. Pat. No. 5,276,231 and U.S. Pat. No. 5,334,793, herein incorporated by reference in its entirety. Aromatics are formed in the dehydrogenation of the $C_{10}$-$C_{12}$-paraffin containing feedstock. As a sorption system is provided, the conditions of dehydrogenation reactor 124 may include those in which benzene and other aromatics are formed. These more severe conditions tend to increase the conversion of paraffins to olefins per pass through dehydrogenation reactor 124.

The olefin-containing effluent from sorption system 154 is passed via line 156 to alkylation reactor 160 for reaction with benzene supplied by line 166 to produce alkylbenzenes. The bottoms from benzene fractionation assembly 164 contain alkylbenzenes and paraffins. Usually the alkylation reactor 160 is operated under conditions such that essentially all of the olefins are reacted. As at least a portion of the detergent range olefin for alkylation is sourced from a $C_5$-$C_6$-containing feedstock, the olefin-containing feed will contain less, and perhaps in some instances, essentially no, similar molecular weight paraffin. Accordingly, the reboiler heat required for recovery of the alkylbenzene product from the alkylation reactor effluent can be appreciably reduced.

The alkylation reaction product is directed by line 162 to benzene fractionation assembly 164 with benzene being recovered as an overhead and recycled to alkylation reactor 160 through line 166. Benzene make-up is provided to benzene fractionation system 164 by line 170. The bottoms stream from benzene fractionation assembly 164 is fed to paraffins fractionation assembly 174 via line 172. The overhead from paraffins fractionation assembly 174 contains paraffins that are recycled to dehydrogenation reactor 140 via line 176. The bottoms fraction from paraffins fractionation assembly 174 is directed via line 178 to heavies fractionation assembly 180 with the purified alkylbenzene being withdrawn as the overhead via line 182 and a heavies-containing bottoms stream being withdrawn via line 184. The heavies-containing bottoms stream may, if desired, be subjected to an additional fractionation to recover additional alkylbenzenes.

Figure 2:
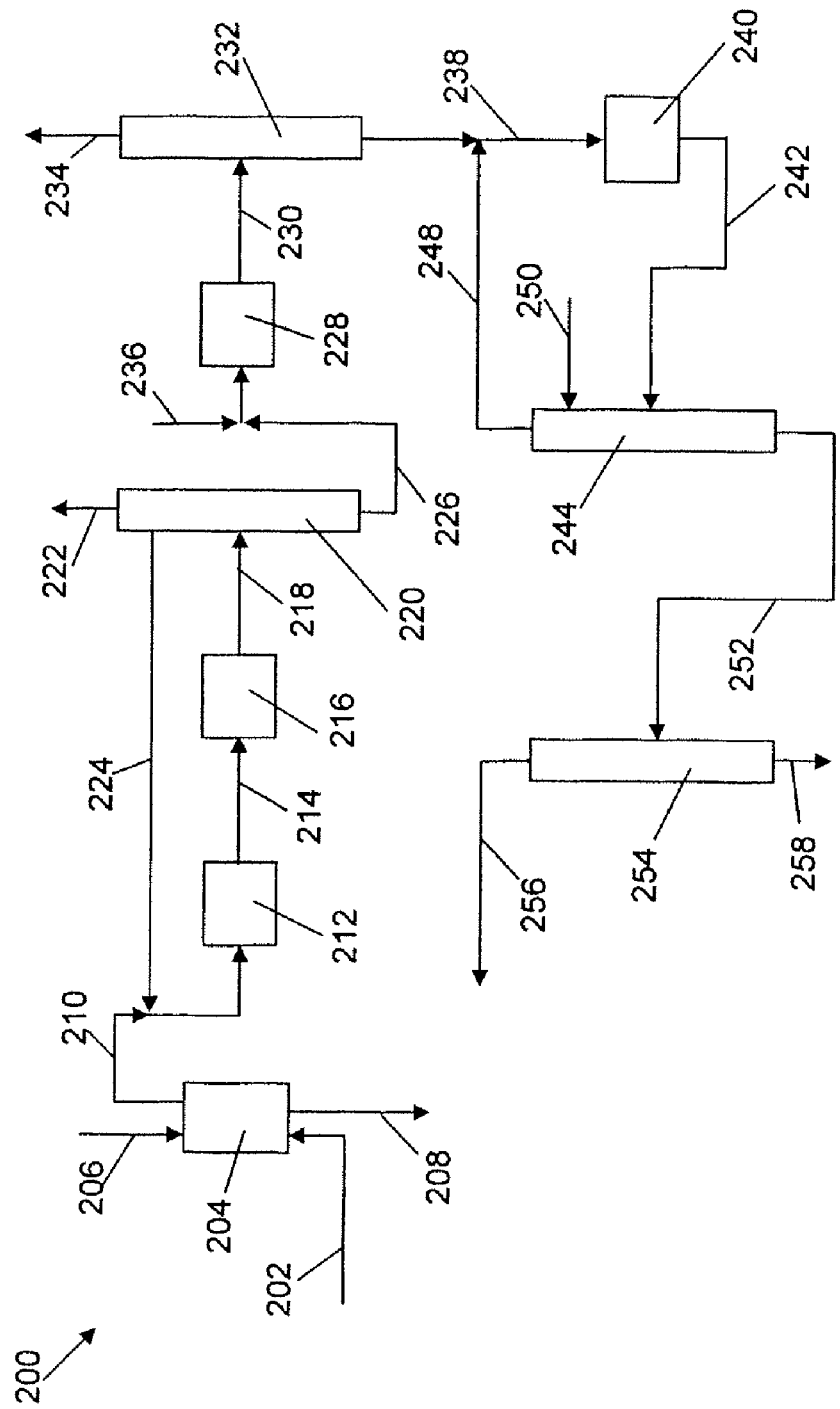
FIG. 2 is a schematic depiction of an apparatus for making alkylbenzenes in which a $C_5$-$C_6$ feed is metathesized to provide a detergent-range olefin stream as a feed to an alkylation reactor.

Turning to FIG. 2, the depicted apparatus uses only a $C_5$-$C_6$-containing feedstock as described in connection with FIG. 1. In apparatus 200, a $C_5$-$C_6$-containing feedstock is provided via line 202 to oxygenate extractor 204. This feedstock may be obtained from any suitable source including a naphtha-range fraction or a Fischer-Tropsch process. For purposes of this discussion, the feedstock is a naphtha range feedstock and contains some higher and lower molecular weight paraffins. A methanol-water sorbent is introduced into extractor 204 via line 206 and the spent sorbent is withdrawn via line 208 for regeneration.

The $C_5$-$C_6$-containing feedstock having oxygenates removed is directed from extractor 204 to dehydrogenation reactor 212 by line 210. The dehydrogenation reactor effluent is then passed via line 214 to metathesis reactor 216 to provide a metathesis reaction product including olefins having from 10 to 12 carbon atoms per molecule. Usually the reaction product contains very little quaternary carbon branching. Advantageously, the metathesis reaction produces little, if any, aromatics. The metathesis product is passed to distillation assembly 220 via line 218. The sought $C_{10}$ to $C_{12}$ olefins are contained in the bottoms stream. An overhead containing hydrogen and low molecular weight hydrocarbons is exhausted via line 222 and the remaining components, primarily paraffins and lower molecular weight olefins, are recycled from distillation assembly 220 to dehydrogenation reactor 212 via line 224.

The bottoms stream is passed through line 226 to selective hydrogenation reactor 228 where diolefins are converted to mono-olefins. The effluent from reactor 228 which contains olefins having a reduced concentration of dienes, is passed via line 230 to stripper 232 for removal of a light-ends-containing overhead by line 234. Depending on the hydrogen and the $C_5$-$C_6$ contents of the overhead, the overhead may be recovered and recycled to selective hydrogenation reactor or the dehydrogenation reactor. Any additional hydrogen required for the selective hydrogenation is supplied by line 236.

Because the olefin-containing feed is essentially devoid of aromatics, the sorption system as described in connection with FIG. 1 is not necessary. Hence, the bottoms fraction from stripper 232 that treats the selective hydrogenation product, is directly fed via line 238 to alkylation reactor 240 for reaction with benzene supplied by line 248.

The alkylation reaction product is directed by line 242 to benzene fractionation assembly 244 with benzene being recovered as an overhead and recycled to alkylation reactor 240 through line 248. Benzene make-up is provided to benzene fractionation system 244 by line 250. The bottoms stream from benzene fractionation assembly 244 is fed via line 252 to heavies fractionation assembly 254 with the purified alkylbenzene being withdrawn as the overhead via line 256 and a heavies-containing bottoms stream being withdrawn via line 258. The heavies-containing bottoms stream may, if desired, be subjected to an additional fractionation to recover additional alkylbenzenes. As the olefins can be essentially-completely consumed in the alkylation reaction and the olefins fed to alkylation reactor 240 contain little, if any, paraffin, the necessity of a paraffins fractionation assembly is obviated. To the extent that paraffins are contained in the olefin feed stream to alkylation reactor 240, they can be passed to the overhead of benzene fractionation assembly 244. A purge can prevent build-up of the paraffins in the alkylation reactor-benzene fractionation assembly loop.

Figure 3:
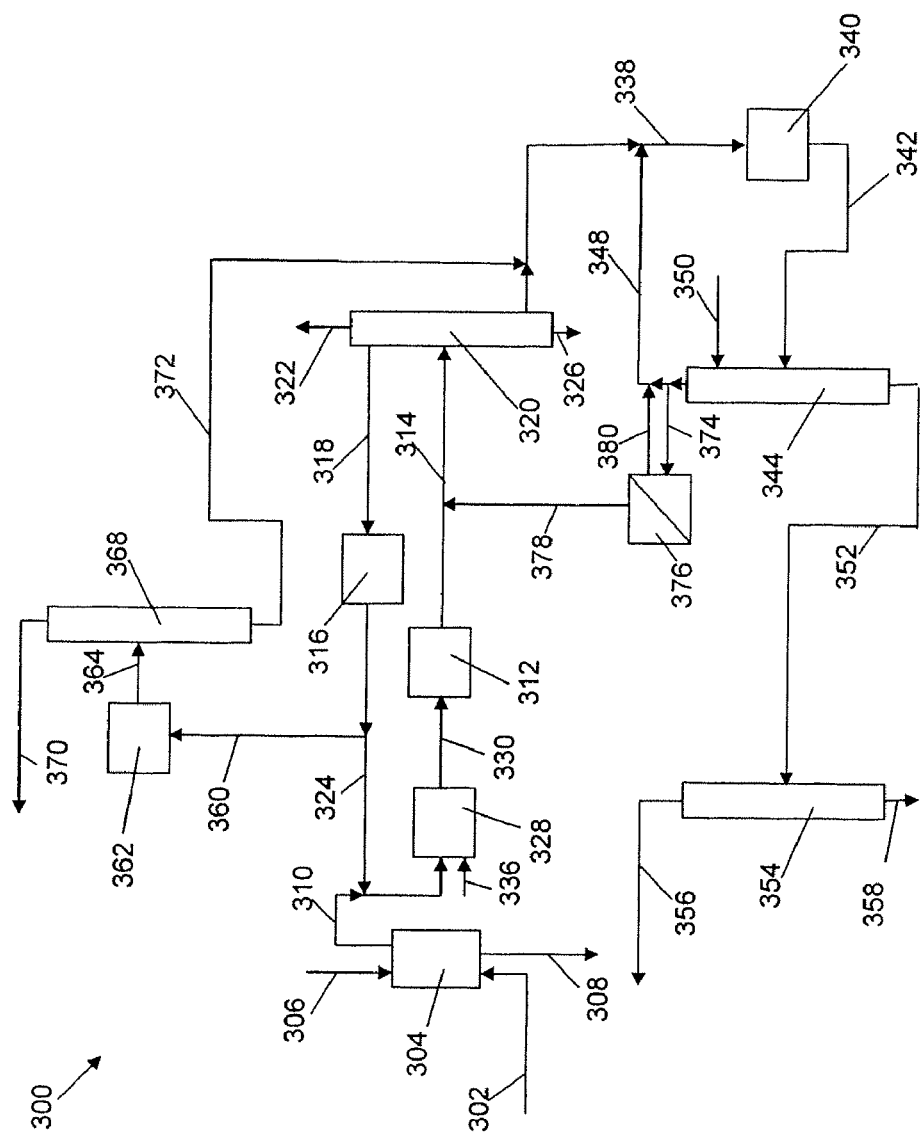
FIG. 3 is a schematic depiction of an apparatus for making alkylbenzenes from a $C_5$-$C_6$ feed with the co-production of benzene during dehydrogenation for use in the alkylation.

In FIG. 3, the depicted apparatus uses an olefin and paraffin-containing feedstock having predominantly hydrocarbons in the $C_5$-$C_6$ range. In apparatus 300, the $C_5$-$C_6$-containing feedstock is provided via line 302 to oxygenate extractor 304. This feedstock may be obtained from any suitable source including a naphtha-range fraction or a Fischer-Tropsch process. For purposes of this discussion, the feedstock is a naphtha range feedstock and contains some higher and lower molecular weight paraffins and olefins. A methanol-water sorbent is introduced into extractor 304 via line 306 and the spent sorbent is withdrawn via line 308 for regeneration.

The $C_5$-$C_6$-containing feedstock having oxygenates removed is directed by line 310 from extractor 304 to selective hydrogenation unit 328 where diolefins are converted to mono-olefins. As will be discussed later, dehydrogenated product is also passed to selective hydrogenation unit 328. Selective hydrogenation unit 328 has a reactor and a stripper for removal of light ends in a stripper overhead. The stripper overhead may be recovered and recycled to the selective hydrogenation reactor or the dehydrogenation reactor, depending on the hydrogen and the $C_5$-$C_6$ contents of the stripper overhead. Make-up hydrogen required for the selective hydrogenation is supplied by line 336. Selective hydrogenation unit 328 removes dienes and any alkynes from the feedstock and from the recycling dehydrogenated product. Advantageously, the olefins in the feedstock are used for the dimerization. By not introducing the feedstock immediately before the dehydrogenation, the olefins in the feedstock do not adversely affect the amount of conversion of paraffin to olefin in the dehydrogenation. This efficient use of valuable olefins in the feedstock is economically advantageous.

The effluent from reactor 328 which contains olefins having a reduced concentration of diolefins is passed via line 330 to dimerization reactor 312 to provide a dimerization reaction product including detergent range olefins. The dimerization reactor effluent is passed to distillation assembly 320 via line 314. The sought detergent range olefins are contained in a higher boiling fraction withdrawn via line 338. A bottoms stream containing trimers and highers is removed via line 326. An overhead containing hydrogen and low molecular weight hydrocarbons is exhausted via line 322 and the remaining components, primarily paraffins, aromatics and lower molecular weight olefins, are withdrawn as a side stream and passed via line 318 to dehydrogenation reactor 316. A dehydrogenated product is withdrawn from dehydrogenation reactor 316 via line 324 and recycled to selective hydrogenation unit 328.

The aromatics are formed during the dehydrogenation. Benzene is the primary aromatic formed, however, some toluene and other alkylaromatics may be formed. A purge is taken via line 360 to maintain the aromatics recycling to the dimerization reactor at a desired concentration. This purge in line 360 is passed to catalytic dealkylation reactor 362 where toluene and other alkylaromatics are dealkylated to form benzene. The dealkylation is conducted under a hydrogen atmosphere. During dealkylation, olefins are hydrogenated. The dealkylated product is passed via line 364 to stripper 368 where an overhead containing lights is withdrawn via line 370 and a bottoms stream containing benzene and paraffins is passed via line 372 to alkylation reactor 340 as discussed further below.

The detergent range olefin fraction from distillation assembly 320 is passed through line 338 to alkylation reactor 340. Because the detergent range olefin fraction is essentially devoid of aromatics, the sorption system as described in connection with FIG. 1 is not necessary. Hence, the fraction is directly fed to alkylation reactor 340 for reaction with benzene supplied by lines 348 and 372. Advantageously, the paraffins co-supplied with benzene via line 372 serve as a heat sink for the exothermic alkylation reaction.

The alkylation reaction product is directed by line 342 to benzene fractionation assembly 344 with benzene being recovered as an overhead and recycled to alkylation reactor 340 through line 348. Benzene make-up is provided to benzene fractionation system 344 by line 350. Since a portion of the benzene for the alkylation reaction is provided by dehydrogenating the feedstock, the amount of benzene make-up provided via line 350 can be significantly reduced. To maintain the paraffins at a desired concentration in alkylation reactor 340, a purge is taken from line 348 by line 374. This purge will be rich in benzene and contain paraffins. As shown, line 374 directs the purge to membrane separator 376 which has a membrane selective for the permeation of acyclic paraffins as compared to benzene. The paraffin-rich permeate is passed via line 378 to distillation assembly 320 such that paraffins can be passed to dehydrogenation reactor 316. A retentate fraction containing benzene is passed via line 380 to alkylation reactor 340. Alternatively, the entire purge stream may be recycled to dehydrogenation reactor 316, or it may be subjected to selective sorption to remove aromatics.

The bottoms stream from benzene fractionation assembly 344 is fed via line 352 to heavies fractionation assembly 354 with the purified alkylbenzene being withdrawn as the overhead via line 356 and a heavies-containing bottoms stream being withdrawn via line 358. The heavies-containing bottoms stream may, if desired, be subjected to an additional fractionation to recover additional alkylbenzenes. As the olefins can be essentially-completely consumed in the alkylation reaction and the olefins fed to alkylation reactor 340 contain little, if any, paraffin, the necessity of a paraffins fractionation assembly is obviated. To the extent that paraffins are contained in the olefin feed stream to alkylation reactor 340, they can be passed to the overhead of benzene fractionation assembly 344. A purge can prevent build-up of the paraffins in the alkylation reactor-benzene fractionation assembly loop.

The invention claimed is:

1. An integrated process for producing detergent range alkylbenzenes from a feedstock predominantly comprising $C_5$ and $C_6$ paraffins, the process comprising:
   a) subjecting the feedstock to dehydrogenation conditions to provide a dehydrogenated product that comprises $C_5$ and $C_6$ mono-olefins and a minor amount of diene;
   b) selectively hydrogenating at least a portion of the dehydrogenated product of step a to reduce diene concentration;
   c) reacting at least a portion of the dehydrogenated product having been subjected to the selective hydrogenation of step b under dimerization or metathesis condition to provide a detergent range olefin product comprising $C_{10}$ to $C_{12}$ mono-olefins;
   d) separating by distillation a refined olefin fraction comprising $C_{10}$ to $C_{12}$ mono-olefins from at least a portion of the detergent range olefin product, the refined olefin fraction containing less than about 0.5 mass-percent paraffins having 9 or more carbon atoms per molecule, and a lower boiling fraction, wherein at least a portion of the lower boiling fraction is recycled to step a;
   e) alkylating benzene with at least a portion of the refined olefin fraction under alkylation conditions including a stoichiometric excess of benzene to olefin to provide an alkylation effluent comprising alkylbenzenes and benzene; and
   f) separating benzene from at least a portion of the alkylation effluent and recycling at least a portion of the separated benzene to step e, wherein the detergent range olefin product of step c contains benzene and non-benzene aromatic compounds and at least a portion of the detergent range olefin product is contacted with a sorbent to selectively sorb the non-benzene aromatic compounds and provide detergent range olefin product having a reduced aromatic compound concentration for step e.

2. The process of claim 1 wherein the alkylation of step e is conducted in the presence of a paraffinic component having between 4 and 7 carbon atoms per molecule.

3. The process of claim 2 wherein the paraffinic component is provided to the alkylation of step e in a mole ratio to olefin of between about 1:1 and 20:1.

4. The process of claim 1 wherein the dehydrogenated product of step a contains aromatic compounds and aromatic compounds are removed from the detergent range olefin product of step c.

5. An integrated process for producing detergent range alkylbenzenes from a feedstock predominantly comprising $C_5$ and $C_6$ paraffins, the process comprising:
   a) subjecting the feedstock to dehydrogenation conditions to provide a dehydrogenated product that comprises $C_5$ and $C_6$ mono-olefins, a minor amount of diene, and a minor amount of cyclics comprising benzene;
   b) selectively hydrogenating at least a portion of the dehydrogenated product of step a to reduce diene concentration;
   c) reacting at least a portion of the dehydrogenated product having been subjected to the selective hydrogenation of step b under dimerization or metathesis condition to provide a detergent range olefin product comprising $C_{10}$ to $C_{12}$ mono-olefins;
   d) separating by distillation a refined olefin fraction comprising $C_{10}$ to $C_{12}$ mono-olefins from at least a portion of the detergent range olefin product, the refined olefin fraction containing less than about 0.1 mass-percent aromatic compounds, and a lower boiling fraction, wherein at least a portion of the lower boiling fraction is recycled to step a;
   e) alkylating benzene with at least a portion of the refined olefin fraction under alkylation conditions including a stoichiometric excess of benzene to olefin to provide an alkylation effluent comprising alkylbenzenes and benzene; and
   f) separating benzene from at least a portion of the alkylation effluent and recycling at least a portion of the separated benzene to step e, wherein the detergent range olefin product of step c contains benzene, and non-benzene aromatic compounds and at least a portion of the detergent range olefin product is contacted with a sorbent to selectively sorb the non-benzene aromatic compounds and provide detergent range olefin product having a reduced aromatic compound concentration for step e.

6. The process of claim 5 wherein aromatic compounds comprise at least about 5 mass-percent of the dehydrogenated product.

7. The process of claim 6 wherein steps a, b, c, and d define a flow cycle loop and wherein a portion of the lower boiling fraction recycled to step a is at least intermittently withdrawn in an amount sufficient to prevent undue build-up of aromatic compounds in the flow cycle loop.

8. The process of claim 7 wherein benzene is recovered from the withdrawn portion, and at least a portion of the recovered benzene is supplied to step e.

9. The process of claim 8 wherein the recovery of benzene is by selective sorption.

10. The process of claim 8 wherein at least a portion of the withdrawn portion is subjected to dealkylation conditions sufficient to provide a dealkylation effluent containing less than about 1 mass-percent toluene based on the mass of benzene in the dealkylation effluent.

11. The process of claim 10 wherein benzene is recovered from the dealkylation effluent, and at least a portion of the benzene recovered from the dealkylation effluent is supplied to step e.

12. The process of claim 11 wherein a fraction containing $C_5$ and $C_6$ paraffins is recovered from the withdrawn portion and at least a portion of the recovered fraction is recycled to step a.

13. The process of claim 12 wherein the recovered fraction containing $C_5$ and $C_6$ paraffins is recovered from the dealkylation effluent.

14. The process of claim 10 wherein the alkylation of step e is conducted in the presence of a paraffinic component having between 4 and 7 carbon atoms per molecule.

15. The process of claim 14 wherein at least a portion of the dealkylation effluent is supplied to step e, the dealkylation conditions are sufficient to hydrogenate olefins, the recovered benzene contains $C_5$ and $C_6$ paraffins, and the $C_5$ and $C_6$ paraffins in the recovered benzene provided to step e provide at least a portion of the paraffinic component.

* * * * *